United States Patent
Sasso et al.

(10) Patent No.: US 11,684,970 B2
(45) Date of Patent: Jun. 27, 2023

(54) IMMERSION SENSOR FOR DETERMINING CHEMICAL COMPOSITION OF MOLTEN METAL

(71) Applicant: VESUVIUS REFRATARIOS LTDA., Rio de Janeiro (BR)

(72) Inventors: Peterney Sasso, Sao Paulo (BR); Ezequias Jose De Souza, Sao Paulo (BR)

(73) Assignee: Vesuvius Refratarios Ltda., Rio de Janeiro (BR)

( * ) Notice: Subject to any disclaimer, the term of this patent is extended or adjusted under 35 U.S.C. 154(b) by 549 days.

(21) Appl. No.: 16/652,497

(22) PCT Filed: Oct. 5, 2018

(86) PCT No.: PCT/US2018/054625
§ 371 (c)(1),
(2) Date: Mar. 31, 2020

(87) PCT Pub. No.: WO2019/071137
PCT Pub. Date: Apr. 11, 2019

(65) Prior Publication Data
US 2020/0269309 A1 Aug. 27, 2020

Related U.S. Application Data

(60) Provisional application No. 62/568,380, filed on Oct. 5, 2017.

(51) Int. Cl.
*B22D 2/00* (2006.01)
*G01N 33/205* (2019.01)
*G01N 27/411* (2006.01)

(52) U.S. Cl.
CPC .......... *B22D 2/00* (2013.01); *G01N 27/4115* (2013.01); *G01N 33/205* (2019.01)

(58) Field of Classification Search
CPC .................................................. G01N 27/4115
See application file for complete search history.

(56) References Cited

U.S. PATENT DOCUMENTS 3,288,589 A * 11/1966 Perry ........................ C21C 5/52
75/508
3,463,005 A 8/1969 Hance
(Continued)

FOREIGN PATENT DOCUMENTS

| CN | 1093804 A | 10/1994 |
| CN | 101158696 A | 4/2008 |

(Continued)

OTHER PUBLICATIONS

Machine translation of DE 3541808 (Kolb) published Feb. 1987.*
(Continued)

*Primary Examiner* — Daniel S Larkin
(74) *Attorney, Agent, or Firm* — MaxGoLaw PLLC

(57) ABSTRACT

An immersion sensor is configured to determine the content of a chemical element in molten metal. The immersion sensor has an auxiliary electrochemical cell extending from an interior surface into the internal volume of a sampling chamber. The sampling chamber can be integrally-formed in a sensor head or in a separate refractory structure. The immersion sensor may be configured for the flow of molten metal into the internal volume of the sampling chamber and into contact with the auxiliary electrochemical cell.

22 Claims, 15 Drawing Sheets

(56) References Cited

U.S. PATENT DOCUMENTS

| | | | |
|---|---|---|---|
| 3,772,177 | A | 11/1973 | Rittiger et al. |
| 4,657,641 | A | 4/1987 | Nakamura et al. |
| 4,830,727 | A | 5/1989 | Sasabe et al. |
| 4,906,349 | A | 3/1990 | Beatrice et al. |
| 5,033,320 | A * | 7/1991 | Baerts ............... G01N 1/125 |
| | | | 374/E13.013 |
| 5,415,052 | A | 5/1995 | Baerts |
| 5,577,841 | A | 11/1996 | Wall |
| 7,141,151 | B2 | 11/2006 | Habets |
| 7,169,274 | B2 | 1/2007 | Habets |
| 7,748,258 | B2 | 7/2010 | Sattmann |
| 8,479,579 | B2 | 7/2013 | Neyens et al. |
| 8,689,650 | B2 * | 4/2014 | Villarreal V ........ G01N 33/205 |
| | | | 73/864.55 |
| 9,116,054 | B2 | 8/2015 | Beyens |
| 9,958,427 | B2 | 5/2018 | Turner et al. |
| 2013/0098173 | A1 * | 4/2013 | Neyens ............. G01N 33/1826 |
| | | | 73/864.51 |

FOREIGN PATENT DOCUMENTS

| | | | | |
|---|---|---|---|---|
| CN | 205449135 U | | 8/2016 | |
| DE | 3541806 C1 | | 2/1987 | |
| EP | 0295112 B1 | | 8/1994 | |
| FR | 2473177 | * | 7/1981 | ............. G01N 25/04 |
| GB | 1271747 A | | 4/1972 | |
| GB | 1283712 A | | 8/1972 | |
| JP | S63273055 A | | 11/1988 | |
| WO | WO-2004048961 A1 | * | 6/2004 | ......... G01N 27/4118 |

OTHER PUBLICATIONS

Machine translation of JP S4844389A published Jun. 9, 1973, 9 pages.*

Machine translation of JP S5365589U published May 14, 1977, 4 pages.*

Machine translation of JP 2002-318225A published Oct. 31, 2002, 19 pages.*

* cited by examiner

IMMERSION SENSOR FOR DETERMINING CHEMICAL COMPOSITION OF MOLTEN METAL

CROSS-REFERENCE TO RELATED APPLICATIONS

This application is a U.S. national stage application, filed under 35 U.S.C. § 371, of International Application No. PCT/US2018/054625, which was filed on 5 Oct. 2018, and which claims priority to U.S. Application No. 62/568,380, filed 5 Oct. 2017, the contents of each of which are incorporated by reference in this specification.

BACKGROUND OF THE INVENTION

(1) Field of the Invention

The present application generally relates to devices for determining the content of various chemical elements in molten metal and alloys.

(2) Description of the Related Art

When melting and refining molten metals and alloys in a liquid state, it can be important to rapidly determine the content of various chemical elements, so that the smelter, steelmaker, or other metallurgist, can proceed with appropriate compositional corrections as quickly as possible, thereby allowing the metallurgist to economically reach a specified compositional quality during production. The determination of certain chemical element levels in molten metals and alloys is currently performed using disposable immersion sensors, which generally comprise a single electrochemical cell.

For example, disposable immersion sensors according to the current state of the art can comprise a cardboard tube that supports a sensor head. The sensor head may contain sensors such as a thermocouple—used to determine the molten metal temperature—and a single electrochemical cell—used to determine the oxygen content and to determine, by correlation, the presence of the other elements in the melt. The sensor head may also contain metallic molds intended to collect samples of the molten metal which will be subsequently analyzed in a laboratory.

The determination of chemical element levels using sensors containing a single electrochemical cell is a known technique, widely used in steel manufacturing and foundry operations. One such sensor, which is often called "an oxygen probe" or "oxygen sensor" in the art, operates according to the Nernst equation, which quantitatively relates oxygen chemical activity in a metal melt (e.g., oxygen partial pressure in the melt) to the electrical potential across the electrochemical cell.

Several patents describe these types of sensors, such as, for example, British Patent No. (GB) 1 283 712 and U.S. Pat. No. 4,906,349, which describe sensors used to determine the oxygen activity in molten metals. Other patents describing oxygen sensors include, for example, British Patent No. (GB) 1 271 747 and U.S. Pat. No. 3,772,177, which describe sensors used for the direct determination of oxygen in molten metals.

Variations of oxygen sensors are also known in the art which possess an auxiliary electrode on the electrochemical cell, the auxiliary electrode containing a chemical element or an oxide of a chemical element to be analyzed. Patents describing such variations include, for example, U.S. Pat. Nos. 4,657,641; 7,141,151; and 7,169,274; and European Patent No. (EP) 0 295 112 B1, which describe sensors used for the determination of silicon in molten metals or alloys.

BRIEF SUMMARY OF THE INVENTION

The invention described in this specification is directed to an immersion sensor to determine chemical element content in molten metal. In one example of the invention, the immersion sensor comprises an auxiliary electrochemical cell located inside a sampling chamber.

In another example of the invention, an immersion sensor comprises a sampling chamber having an internal volume formed in a refractory material, and an auxiliary electrochemical cell extending from an interior surface into the internal volume of the sampling chamber. The immersion sensor is configured for the flow of molten metal into the internal volume of the sampling chamber and into contact with the auxiliary electrochemical cell.

In another example of the invention, an immersion sensor comprises a sensor head, a sampling chamber having an internal volume formed in a refractory material, an auxiliary electrochemical cell extending from an interior surface into the internal volume of the sampling chamber, and an inlet channel extending between the internal volume of the sampling chamber and a volume external to the immersion sensor. The immersion sensor is configured for the flow of molten metal from the external volume, through the inlet channel, into the internal volume of the sampling chamber, and into contact with the auxiliary electrochemical cell.

BRIEF DESCRIPTION OF THE DRAWINGS

Various features and characteristics of the invention described in this specification may be more thoroughly understood by reference to the accompanying figures. It is understood that the drawings are schematic, not necessarily to scale, and that features and characteristics that are not required for understanding the invention described in this specification may have been omitted for clarity.

Figure 1:
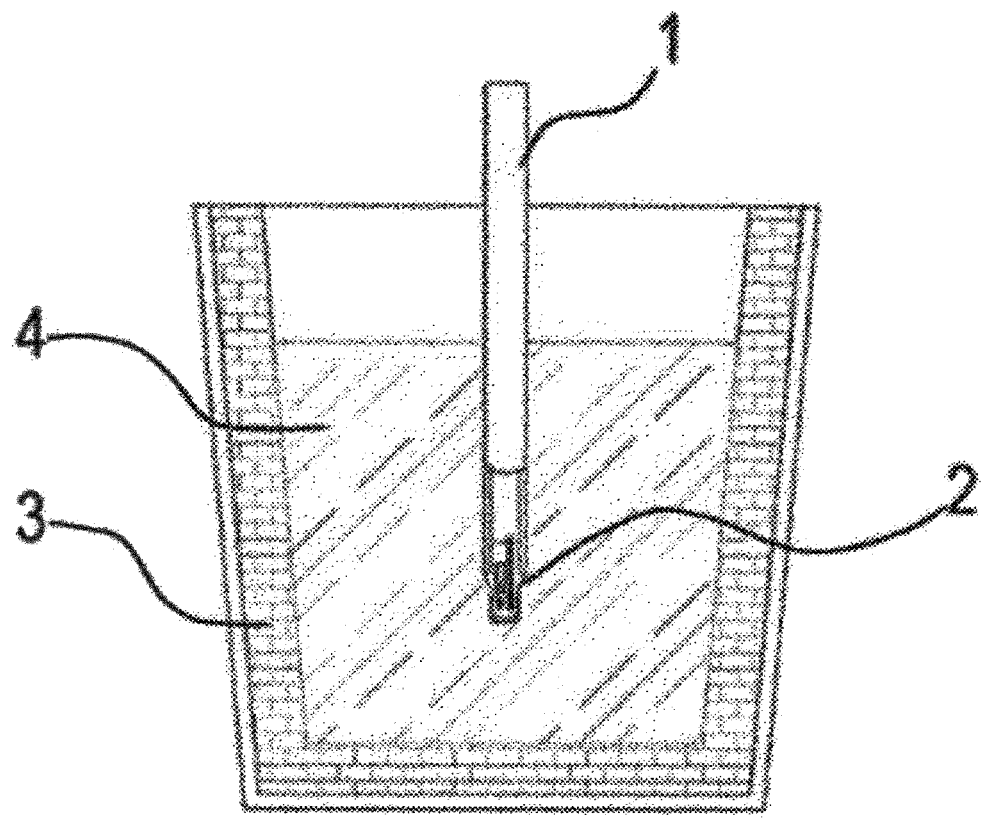
FIG. 1 is a side elevational view in cross-section of a state of the art immersion sensor immersed in molten metal in a metallurgical vessel.

The reader will appreciate the foregoing features and characteristics, as well as others, upon considering the following detailed description of the invention.

DETAILED DESCRIPTION OF THE INVENTION

As used in the specification, including the claims, the term "distal," and variations thereof, means located toward the immersion end of an immersion sensor, and the term "proximal," and variations thereof, means located away from the immersion end of an immersion sensor. The terms "distal" and "proximal," and variations thereof, are descriptive terms of relative location along the immersion direction of an immersion sensor, which, for example, generally corresponds to the length dimension of an elongated immersion sensor assembly comprising a sensor head and a carrier tube.

As used in this specification, including the claims, the term "metal" includes both elemental metals and metallic alloys comprising a base metal and one or more metallic or non-metallic alloying elements added to the base metal. Also, as used in this specification, including the claims, and unless otherwise specified, the terms "upper," "lower," "upward," "downward," "above," "below", and variations thereof, and the like, relate to the orientations shown in the drawings, and are used for ease of description, and do not limit the invention to use in any specific orientation.

Conventional immersion sensors and probes generally comprise an electrochemical cell externally mounted on the immersion end (i.e., the distal end) of a sensor head. In this location, the electrochemical cell is exposed to a large amount of molten metal during the measurement, thus limiting the use of the sensor and the efficiency of the measurement. Likewise, the ability to maintain an auxiliary electrode coating applied on the electrochemical cell is compromised by the exposure to the bulk metal melt during measurement.

The limitation and the efficiency of the measurement, and the compromised maintenance of the auxiliary electrode coating when applied to conventional sensors, is due to the position of the electrochemical cell on the immersion end (i.e., the distal end) of the sensor head, where the electrochemical cell is subject to the aggressive environment to which it is exposed, including high temperatures, molten metal flow velocity, agitation and turbulence during the measurement, and also the large amount of liquid metal mass surrounding the electrochemical cell.

The immersion sensor of the present invention addresses these issues and can be used to analyze the content of a chemical element of interest to a smelter, steelworker, or other metallurgist, through the use of an auxiliary electrochemical cell, based on an oxygen-measuring electrochemical cell, located inside a sampling (i.e., sample collection) chamber formed in the structure of the immersion sensor. The location of the auxiliary electrochemical cell inside the sampling chamber facilitates the determination of the oxygen level in the molten metal in a less aggressive environment, beginning as the molten metal flows into the sampling chamber and until the molten metal solidifies inside the sampling chamber.

The location of the auxiliary electrochemical cell inside a sampling chamber reduces or eliminates the problems associated with the aggressive environment of the bulk metal melt (e.g., contact with a large melt volume, contact with a large thermal mass, and contact with melt agitation, turbulence, and flow). The sampling chamber provides a relatively small volume into which the molten metal flows and contacts the auxiliary electrochemical cell, which provides for decreased melt volume, thermal mass, and melt fluid velocity in contact with the auxiliary electrochemical cell compared to an exterior distal end position on an exposed sensor head. Additionally, the relatively small sampling chamber volume facilitates a rapid decrease in the temperature of the in-flowing molten metal, which accelerates solidification and maintains in place during measurement any auxiliary electrode coating located on the electrochemical cell, thereby maximizing the measurement efficiency of the sensor.

As used in this specification, including the claims, the term "auxiliary electrochemical cell" means an electrochemical cell configured to determine the content of a chemical element in molten metal in contact with the exterior surface of the electrochemical cell. See, for example, the electrochemical cells described in GB-1283712; U.S. Pat No. 4,906,349; GB-1271747; U.S. Pat. Nos. 3,772,177; 4,657,641; 7,141,151; 7,169,274; and EP-0295112-B1, which are incorporated by reference into this specification. An auxiliary electrochemical cell can, but need not, comprise a coating located on at least a portion of an exterior surface of the auxiliary electrochemical cell. Such an "auxiliary electrode coating," if present on an exterior surface of an electrochemical cell configured to determine the content of oxygen in a metal melt, can facilitate the determination of the content of non-oxygen chemical elements in the metal melt.

Accordingly, the present invention relates to an auxiliary electrochemical cell for oxygen determination, coated or uncoated with an auxiliary electrode coating, located within a sampling chamber formed in an immersion sensor, which sampling chamber will receive the molten metal when immersed in a metal melt. The auxiliary electrochemical cell can then analyze the oxygen level in the received molten metal, beginning when the molten metal enters the sampling chamber and contacts the auxiliary electrochemical cell and proceeding during the cooling and solidification of the molten metal in the sampling chamber. In this manner, it is possible, through empirical statistical formulas, for example, to determine the content of chemical elements of interest contained in a metal melt to a smelter, steelworker, or other metallurgist. Such chemical elements of interest can include, for example, oxygen, carbon, silicon, manganese, phosphorus, sulfur, aluminum, copper, chromium, molybdenum, nickel, boron, calcium, lead, tin, titanium, niobium, cobalt, iron, vanadium, tungsten, magnesium, zinc, zirconium, antimony, and the like, and oxides of these elements.

The immersion sensor of this invention can be used to determine the content of an element of interest in any type of molten metal, such as, for example, iron and its alloys (including steels), aluminum and its alloys, copper and its alloys, chromium and its alloys, molybdenum and its alloys, nickel and its alloys, lead and its alloys, tin and its alloys, titanium and its alloys, niobium and its alloys, cobalt and its alloys, vanadium and its alloys, tungsten and its alloys, magnesium and its alloys, zirconium and its alloys, zinc and its alloys, antimony and its alloys, manganese and its alloys, and the like.

Figure 24:
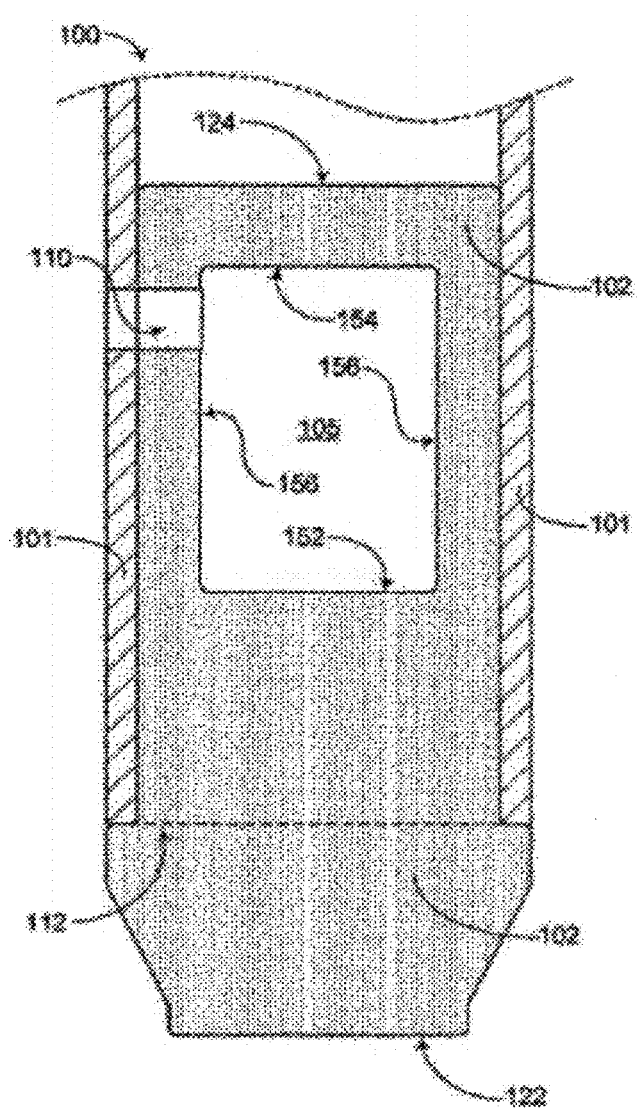
FIG. 24 is a cross-sectional diagram of an immersion sensor illustrating the relative location of a sensor head comprising an integral sampling chamber.
Figure 25:
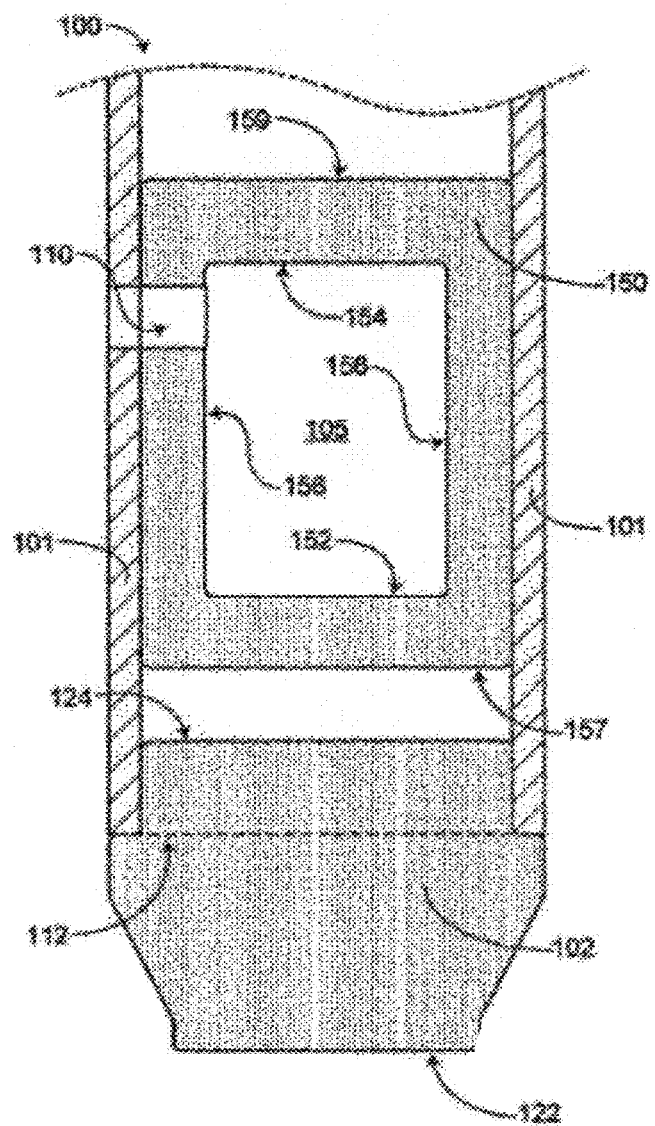
FIG. 25 is a cross-sectional diagram of an immersion sensor illustrating the relative location of a sensor head and a separate refractory structure, not contiguous with the sensor head, comprising an integral sampling chamber.

Referring to FIGS. 24 and 25, an immersion sensor 100 comprises a sensor head 102 located on the distal end 112 of a carrier tube 101. The sensor head 102 can comprise a structure made of a refractory material such as, for example, molded foundry/casting sand, alumina, or the like. The carrier tube 101 is shown as a single structure, which can comprise a material of construction such as, for example, cardboard, plastic, metal, or the like. It is also understood that the carrier tube 101 could comprise multiple components, such as, for example, a metal or plastic tube surrounded by a cardboard or paper sleeve. The sensor head 102 comprises a distal (lower/immersion) end 122 and a proximal (upper) end 124. The proximal end 124 of the sensor head 102 is inserted into the interior lumen of the carrier tube 101 through the distal end 112 of the carrier tube 101. The distal end 122 of the sensor head 102 is exposed to and contacts molten metal during use. Electrochemical cells, thermocouples, or other sensors, and sensor electrodes, contacts, and connections are omitted for clarity from FIGS. 24 and 25.

Referring to FIG. 24, the sensor head 102 comprises an integrally-formed sampling chamber 105. The sampling chamber 105 is located proximal to the distal end 122 of the sensor head 102, and the sampling chamber 105 is located distal to the proximal end 124 of the sensor head 102. Referring to FIG. 25, the immersion sensor 100 comprises the sensor head 102 and a separate refractory structure 150. The refractory structure 150 can comprise a refractory material of construction such as, for example, molded foundry/casting sand, alumina, or the like. The refractory structure 150 is located in the interior lumen of the carrier tube 101, proximal to the proximal end 124 of the sensor head 102. The refractory structure 150 comprises a distal (lower) end 157 and a proximal (upper) end 159. The refractory structure 150 also comprises an integrally-formed sampling chamber 105. The sampling chamber 105 is located proximal to the distal end 157 of the refractory structure 150, and the sampling chamber 105 is located distal to the proximal end 159 of the refractory structure 150.

Referring again to FIGS. 24 and 25, the sampling chamber 105 comprises a distal (lower) interior surface 152, a proximal (upper) interior surface 154, and lateral interior surfaces 156. The internal volume of the sampling chamber 105 is in fluid communication with the volume external to the immersion sensor 100 through an inlet channel 110. The inlet channel 110 extends from one lateral interior surface 156 of the sampling chamber 105 to a lateral exterior surface of the sensor head 102 or the refractory structure 150, as applicable. An aperture in the carrier tube 101 is aligned with the inlet channel 110 to provide the fluid communication between the internal volume of the sampling chamber 105 and the volume external to the immersion sensor 100.

FIG. 1 illustrates an immersion sensor in use. The immersion sensor comprises a sensor head 2 located on the distal end of a carrier tube 1. The immersion sensor is immersed in molten metal 4 in a metallurgical vessel 3 (e.g., a ladle, a convertor, or any other type of metallurgical vessel configured to receive and/or process molten metal). The sensor head 2 comprises sensors such as, for example, a thermocouple and/or an electrochemical cell and/or a metallic mold configured to collect a metal sample, which can be subsequently analyzed in a laboratory, for example. The sensors are located on the distal end of the sensor head 2.

Figure 2:
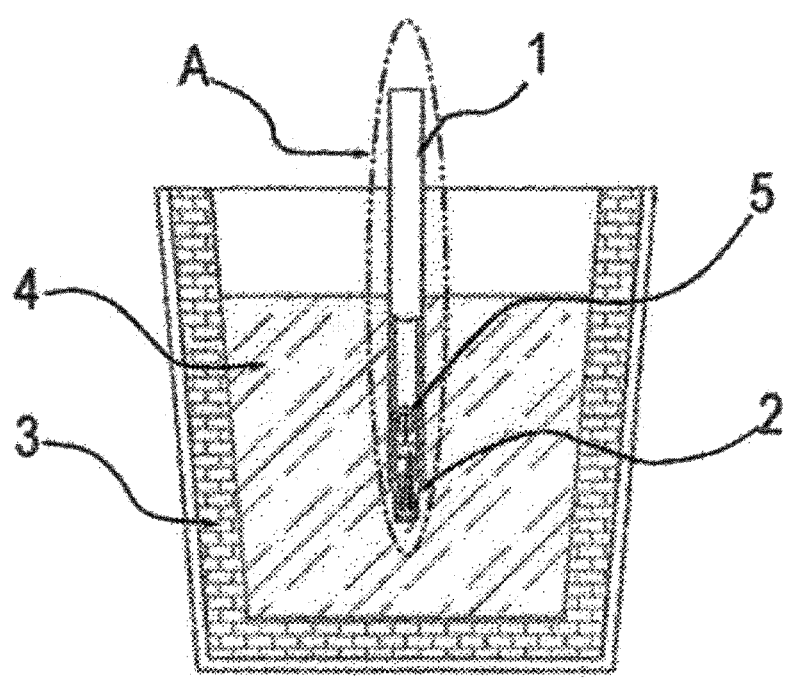
FIG. 2 is a side elevational view in cross-section of an immersion sensor according to the present invention immersed in molten metal in a metallurgical vessel.

FIG. 2 illustrates an immersion sensor A in use in accordance with the present invention. The immersion sensor A comprises a sensor head 2 located on the distal end of a carrier tube 1. The immersion sensor A is immersed in molten metal 4 in a metallurgical vessel 3 (e.g., a ladle, a convertor, or any other type of metallurgical vessel configured to receive and/or process molten metal). The sensor head 2 comprises sensors such as, for example, a thermocouple and/or an electrochemical cell and/or a metallic mold configured to collect a metal sample, which can be subsequently analyzed in a laboratory, for example. The sensors are located on the distal end of the sensor head 2. The carrier tube 1 is shown as a single structure, which can comprise a material of construction such as, for example, cardboard, plastic, metal, or the like. It is also understood that the carrier tube 1 could comprise multiple components, such as, for example, a metal or plastic tube surrounded by a cardboard or paper sleeve.

The immersion sensor A also comprises a separate refractory structure, not contiguous with sensor head 2, comprising an internal sampling chamber 5. The separate refractory structure containing the internal sampling chamber 5 is located proximal to the sensor head 2. The sampling chamber 5 comprises an auxiliary electrochemical cell extending into the sampling chamber from an interior surface of the sampling chamber. The sensor head 2 and the refractory structure containing the sampling chamber 5 can independently comprise a refractory material of construction, such as, for example, molded foundry/casting sand, alumina, or the like. Additionally, the sampling chamber can comprise a material of construction selected from the group consisting of metallic materials, ceramic materials, and cermet materials, and combinations of any thereof. For example, the sampling chamber can be formed in a refractory structure made of a metallic material, ceramic material, or cermet material, or combination material.

Figure 3:
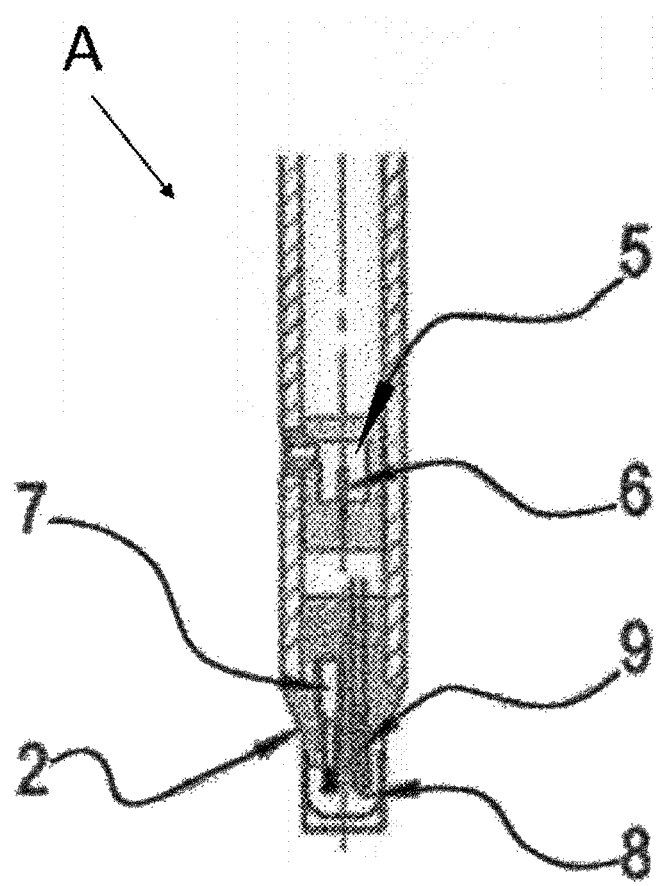
FIG. 3 is a side elevational view in cross-section of the immersion sensor shown in FIG. 2 and illustrating certain components of the immersion sensor.

FIG. 3 further illustrates the immersion sensor A in accordance with the present invention. The sensor head 2 is shown comprising a principal electrochemical cell 8 and a thermocouple 9 located on the distal end of the sensor head 2. The sensor head 2 also comprises a metallic mold 7 formed in the sensor head 2. The metallic mold 7 is configured to collect samples of molten metal 4 (see FIG. 2) to be subsequently analyzed in a laboratory. An auxiliary electrochemical cell 6 is located in the sampling chamber 5 and extends into the internal volume of the sampling chamber 5. The auxiliary electrochemical cell may be negative with respect to another electrical contact to the sampling chamber and may communicate with or function as a negative contact. A metallic electrode extending into the sampling chamber (not shown), a metallic coating on at least a portion of an interior surface of the sampling chamber (not shown), or a metallic mold, may communicate with or function as a positive contact of the auxiliary electrochemical cell.

Figure 4:
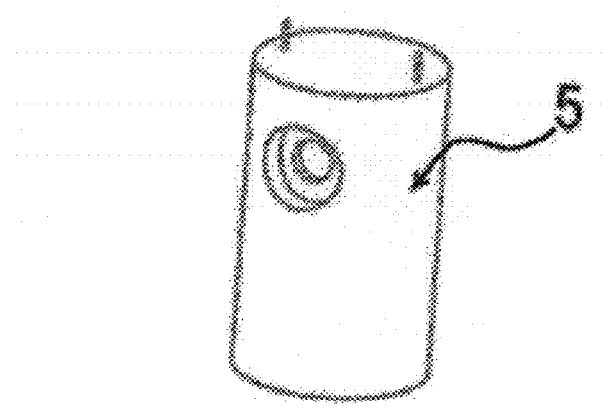
FIG. 4 is a perspective view of the exterior of a sampling chamber comprising an auxiliary electrochemical cell.

FIG. 4 shows the exterior surfaces of the separate refractory structure comprising the sampling chamber 5 formed within the refractory structure. Although not shown, the auxiliary electrochemical cell 6 is located in the internal sampling chamber 5.

Figure 5:
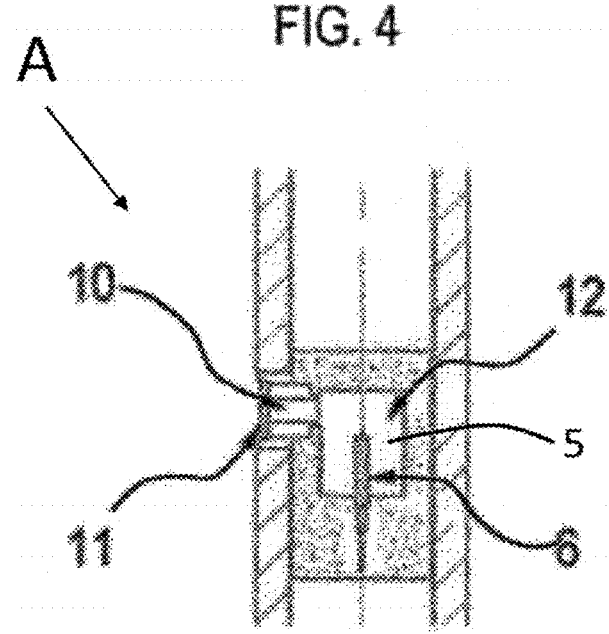
FIG. 5 is a side elevational view in cross-section of the sampling chamber shown in FIG. 4, located within a carrier tube, and illustrating the auxiliary electrochemical cell extending into the sampling chamber from the distal interior surface of the sampling chamber.

FIG. 5 further illustrates the refractory structure comprising the sampling chamber 5 of the immersion sensor A. The auxiliary electrochemical cell 6 extends from a distal interior surface into the internal volume 12 of the sampling chamber 5. The internal volume 12 of the sampling chamber 5 can range from 5 $cm^3$ to 50 $cm^3$, or any sub-range subsumed therein, such as, for example, 5-25 $cm^3$, 10-50 $cm^3$, or 15-45 $cm^3$. An inlet channel 10 extends from a lateral interior surface of the internal volume 12 of the sampling chamber 5 to an exterior surface of the immersion sensor A. The inlet channel 10 provides fluid communication between the internal volume 12 of the sampling chamber 5 and a volume external to the immersion sensor A. In use, molten metal flows from the external volume, through the inlet channel 10, and into the internal volume 12 of the sampling chamber 5, where the molten metal contacts the auxiliary electrochemical cell 6 and the content of a chemical element in the molten metal is determined.

A protective cap or other temporary barrier structure 11 is located in the inlet channel 10 and functions to prevent slag from entering into the internal volume 12 of the sampling chamber 5 by temporarily blocking the inlet channel 10 during immersion of the immersion sensor A into a metal melt. After the exterior opening of the inlet channel 10 passes through a slag layer and contacts molten metal, the protective cap or other temporary barrier structure 11—which can comprise paper, cardboard, plastic, metal/alloy, or another fugitive material or combinations of materials—burns, melts, or is otherwise removed, thereby unblocking the inlet channel 10 and allowing molten metal to flow into the internal volume 12 of the sampling chamber 5.

Figure 6:
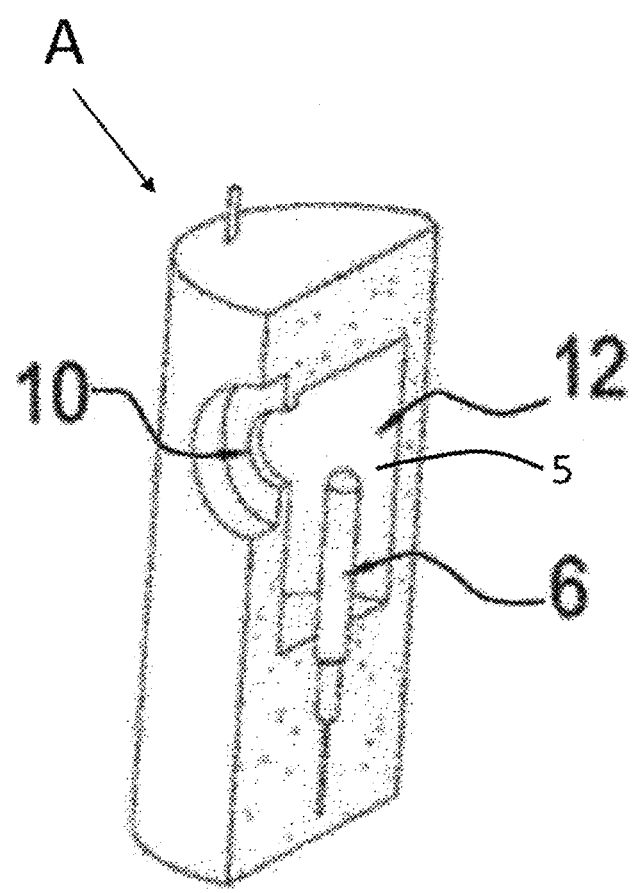
FIG. 6 is a perspective view in cross-section of the sampling chamber shown in FIG. 4 and illustrating the auxiliary electrochemical cell extending into the sampling chamber from the distal interior surface of the sampling chamber.

FIG. 6 further illustrates the refractory structure comprising the sampling chamber 5 of the immersion sensor A. The auxiliary electrochemical cell 6 extends from a distal interior surface into the internal volume 12 of the sampling chamber 5. An inlet channel 10 extends from a lateral interior surface of the internal volume 12 of the sampling chamber 5 to an exterior surface of the refractory structure. In use, molten metal flows through the inlet channel 10 and into the internal volume 12 of the sampling chamber 5, where the molten metal contacts the auxiliary electrochemical cell 6 and the content of a chemical element in the molten metal is determined.

Figure 7:
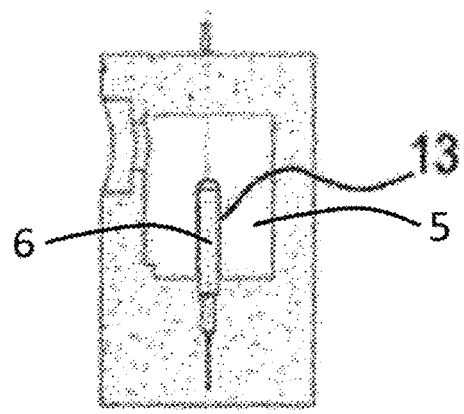
FIG. 7 is a side elevational view in cross-section of a sampling chamber comprising an auxiliary electrochemical cell extending into the sampling chamber from the distal interior surface of the sampling chamber, the auxiliary electrochemical cell comprising a coating located on at least a portion of the exterior surface of the auxiliary electrochemical cell.

FIG. 7 shows an auxiliary electrode coating 13 located on at least a portion of an exterior surface of the auxiliary electrochemical cell 6. As described above, the auxiliary electrode coating 13 can comprise any metal or metallic compound, such as a metallic oxide, that provides the ability to determine the content of a chemical element of interest in molten metal that enters the sampling chamber 5 and contacts the auxiliary electrode coating 13 on the auxiliary electrochemical cell 6.

Figure 8:
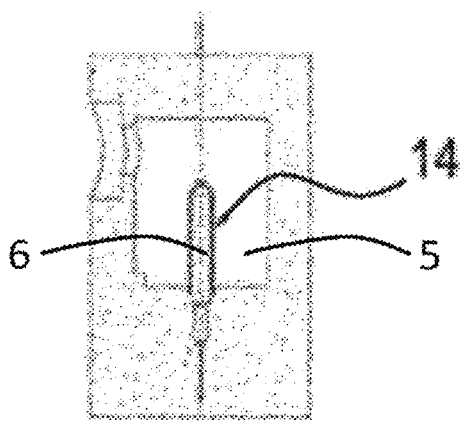
FIG. 8 is a side elevational view in cross-section of a sampling chamber comprising an auxiliary electrochemical cell extending into the sampling chamber from the distal interior surface of the sampling chamber, the auxiliary electrochemical cell comprising a metallic coating located on at least a portion of the exterior surface of the auxiliary electrochemical cell and functioning as a thermal shock shield that protects the auxiliary electrochemical cell from thermal shock damage upon initial contact with molten metal flowing into the sampling chamber.

FIG. 8 shows a metallic coating 14 located on at least a portion of an exterior surface of the auxiliary electrochemical cell 6. The metallic coating 14 functions as a thermal shock shield that protects the auxiliary electrochemical cell 6 from thermal shock damage upon initial contact with molten metal flowing into the sampling chamber 5. In use, when the molten metal enters the sampling chamber 5, the metallic coating 14 melts and the molten metal then contact contacts the underlying exterior surface of the auxiliary electrochemical cell 6, which can optionally comprise an auxiliary electrode coating 13, as shown in FIG. 7, in which case the molten metal contacts the auxiliary electrode coating 13.

Figure 9:
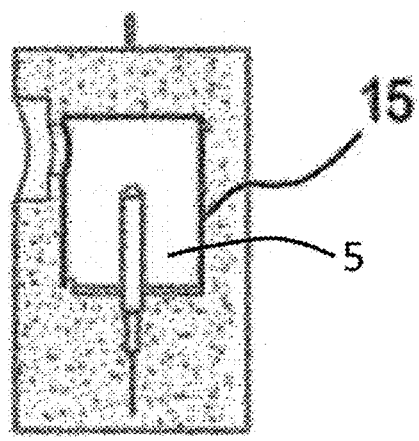
FIG. 9 is a side elevational view in cross-section of a sampling chamber comprising an auxiliary electrochemical cell extending into the sampling chamber from the distal interior surface of the sampling chamber, the sampling chamber further comprising a ceramic coating located on at least a portion of an interior surface of the sampling chamber.

FIG. 9 shows a ceramic coating or glazing 15 located on at least a portion of an interior surface of the sampling chamber 5. The ceramic coating or glazing 15 functions to reduce or eliminate contamination of the molten metal to be analyzed from the refractory material forming the refractory structure comprising the internal sampling chamber 5.

Figure 10:
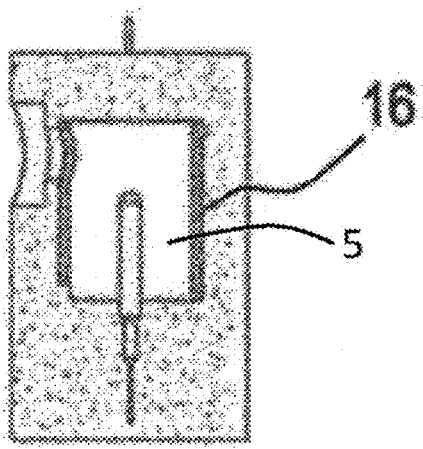
FIG. 10 is a side elevational view in cross-section of a sampling chamber comprising an auxiliary electrochemical cell extending into the sampling chamber from the distal interior surface of the sampling chamber, the sampling chamber further comprising a metallic coating located on at least a portion of an interior surface of the sampling chamber.

FIG. 10 shows a metallic coating 16 located on at least a portion of an interior surface of the sampling chamber 5. The metallic coating 16 can function as a cooling element that absorbs heat from the molten metal entering the sampling chamber 5. The metallic coating 16 can melt upon contact and accelerate the cooling rate and solidification of the molten metal entering the sampling chamber 5.

Figure 11:
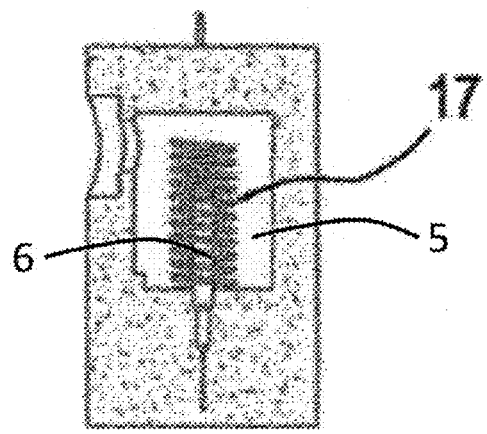
FIG. 11 is a side elevational view in cross-section of a sampling chamber comprising an auxiliary electrochemical cell extending into the sampling chamber from the distal interior surface of the sampling chamber, and a deoxidizing material located adjacent to the exterior surface of the auxiliary electrochemical cell.

FIG. 11 shows a deoxidizing material 17 located adjacent to the exterior surface of the auxiliary electrochemical cell 6 in the sampling chamber 5. The deoxidizing material 17 functions to remove free oxygen from the molten metal to be analyzed by the auxiliary electrochemical cell 6. The deoxidizing material can be selected, for example, from the group consisting of aluminum, aluminum alloys, titanium, titanium alloys, zirconium, and zirconium alloys, and combinations of any thereof.

Figure 12:
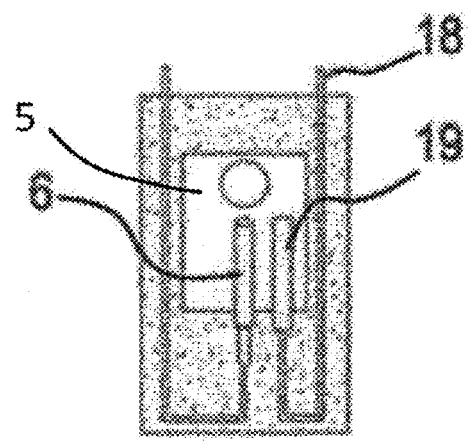
FIG. 12 is a side elevational view in cross-section of a sampling chamber comprising an auxiliary electrochemical cell extending into the sampling chamber from the distal interior surface of the sampling chamber, and an electrode extending into the sampling chamber from the distal interior surface of the sampling chamber, wherein the electrode functions as a positive contact of the auxiliary electrochemical cell.

FIG. 12 shows the auxiliary electrochemical cell 6 and a metallic electrode 19 extending into the sampling chamber 5 from a distal interior surface. The metallic electrode 19 functions as a positive contact 18 of the auxiliary electrochemical cell 6.

Figure 13:
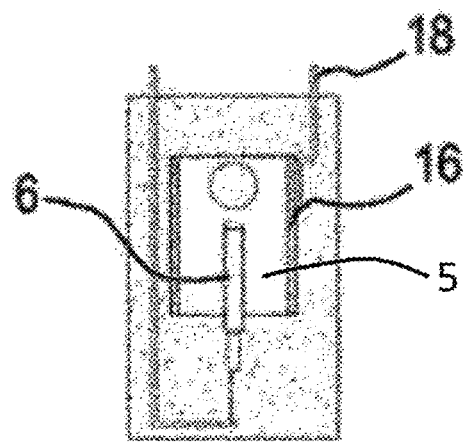
FIG. 13 is a side elevational view in cross-section of a sampling chamber comprising an auxiliary electrochemical cell extending into the sampling chamber from the distal interior surface of the sampling chamber, the sampling chamber further comprising a metallic coating located on at least a portion of an interior surface of the sampling chamber, wherein the metallic coating functions as a positive contact of the auxiliary electrochemical cell.

FIG. 13 shows a metallic coating 16 located on at least a portion of an interior surface of the sampling chamber 5. The metallic coating 16 functions as a positive contact 18 of the auxiliary electrochemical cell 6.

Figure 14:
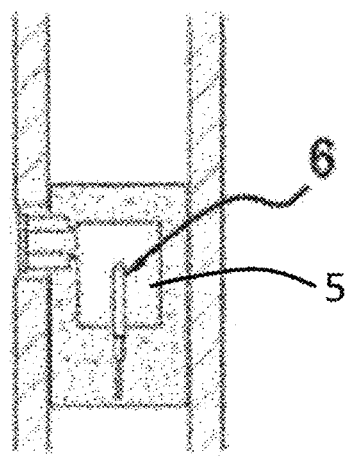
FIG. 14 is a side elevational view in cross-section of a sampling chamber located within a carrier tube, the sampling chamber comprising an auxiliary electrochemical cell extending into the sampling chamber from the distal interior surface of the sampling chamber.
Figure 15:
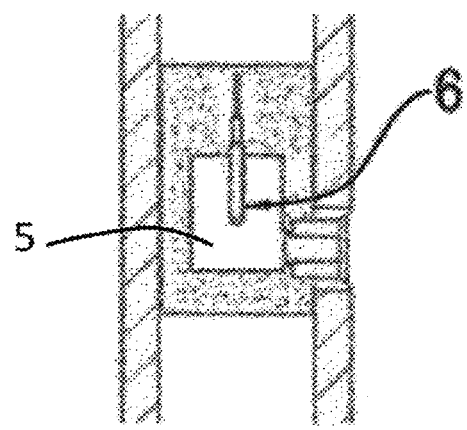
FIG. 15 is a side elevational view in cross-section of a sampling chamber located within a carrier tube, the sampling chamber comprising an auxiliary electrochemical cell extending into the sampling chamber from the proximal interior surface of the sampling chamber.
Figure 16:
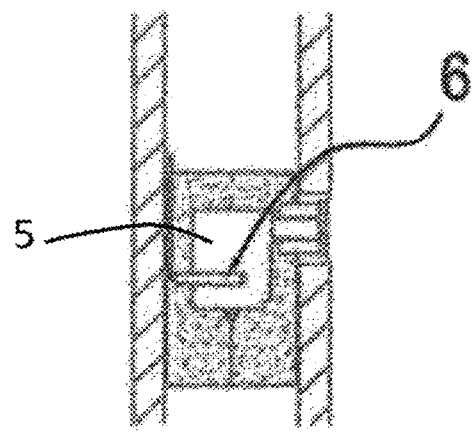
FIG. 16 is a side elevational view in cross-section of a sampling chamber located within a carrier tube, the sampling chamber comprising an auxiliary electrochemical cell extending into the sampling chamber from a lateral interior surface of the sampling chamber.

FIG. 14 shows the auxiliary electrochemical cell 6 extending from a distal interior surface into the sampling chamber 5. FIG. 15 shows the auxiliary electrochemical cell 6 extending from a proximal interior surface into the sampling chamber 5. FIG. 16 shows the auxiliary electrochemical cell 6 extending from a lateral interior surface into the sampling chamber 5. Accordingly, FIGS. 14-16 show the auxiliary electrochemical cell 6 in a lower position, an upper position, and a lateral position, respectively.

Figure 17:
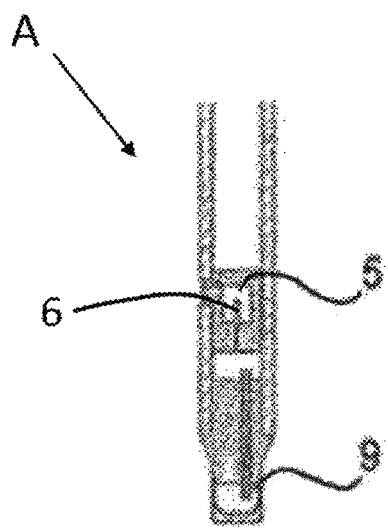
FIG. 17 is a side elevational view in cross-section of an immersion sensor comprising a sensor head located on the distal end of a carrier tube, the sensor head comprising a thermocouple. The immersion sensor further comprises a sampling chamber located proximal to the sensor head, the sampling chamber comprising an auxiliary electrochemical cell extending into the sampling chamber, wherein the sampling chamber is formed in a refractory structure that is separate from, or not contiguous with, the sensor head.

FIG. 17 shows the immersion sensor A comprising a sensor head located on the distal end of a carrier tube, the sensor head comprising a thermocouple 9. The immersion sensor A also comprises a separate refractory structure, not contiguous with the sensor head, comprising the sampling chamber 5. The separate refractory comprising the sampling chamber 5 is located proximal to the sensor head. The auxiliary electrochemical cell 6 extends into the sampling chamber 5, as described above. A sensor head distal end cap shields thermocouple 9 until the cap burns, melts, or is otherwise removed. The outer portion of the sensor head distal end cap may comprise cardboard; the inner portion of the sensor head distal end cap may comprise steel.

Figure 18:
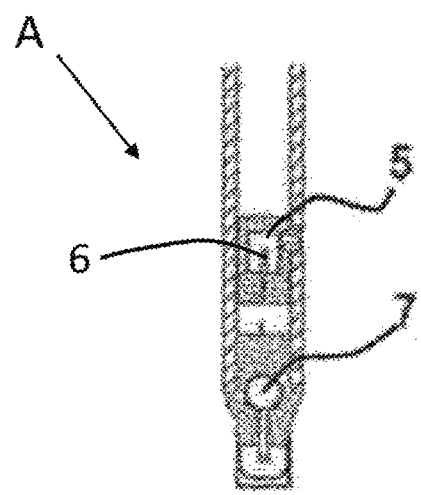
FIG. 18 is a side elevational view in cross-section of an immersion sensor comprising a sensor head located on the distal end of a carrier tube, the sensor head comprising a metallic mold configured to collect samples of molten metal. The immersion sensor further comprises a sampling chamber located proximal to the sensor head, the sampling chamber comprising an auxiliary electrochemical cell extending into the sampling chamber, wherein the sampling chamber is formed in a refractory structure that is separate from, or not contiguous with, the sensor head.

FIG. 18 shows the immersion sensor A comprising a sensor head located on the distal end of a carrier tube, the sensor head comprising a metallic mold 7. The immersion sensor A also comprises a separate refractory structure, not contiguous with the sensor head, comprising the sampling chamber 5. The separate refractory structure comprising the sampling chamber 5 is located proximal to the sensor head. The metallic mold 7 is configured to collect samples of molten metal. The auxiliary electrochemical cell 6 extends into the sampling chamber 5, as described above. A sensor head distal end cap shields metallic mold 7 until the cap burns, melts, or is otherwise removed. The outer portion of the sensor head distal end cap may comprise cardboard; the inner portion of the sensor head distal end cap may comprise steel.

Figure 19:
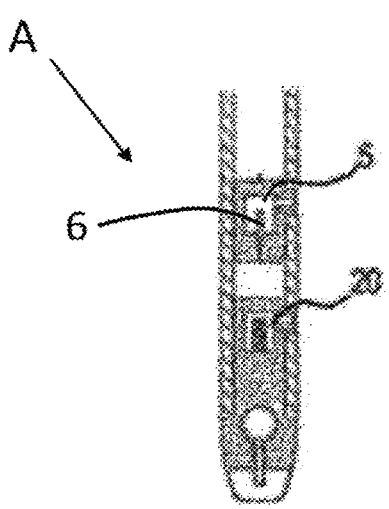
FIG. 19 is a side elevational view in cross-section of an immersion sensor comprising a sensor head located on the distal end of a carrier tube, the sensor head comprising a metallic mold configured to collect samples of molten metal, and a thermal analysis chamber integrally-formed in a proximal portion of the sensor head. The immersion sensor further comprises a sampling chamber located proximal to the sensor head, the sampling chamber comprising an auxiliary electrochemical cell extending into the sampling chamber, wherein the sampling chamber is formed in a refractory structure that is separate from, or not contiguous with, the sensor head.

FIG. 19 shows the immersion sensor A comprising a sensor head located on the distal end of a carrier tube, the sensor head comprising a metallic mold configured to collect samples of molten metal, and also comprising a thermal analysis chamber 20 integrally-formed in the sensor head in a location proximal to the metallic mold. The immersion sensor A also comprises a separate refractory structure, not contiguous with the sensor head, comprising the sampling chamber 5. The separate refractory structure comprising the sampling chamber 5 is located proximal to the sensor head comprising the thermal analysis chamber 20. The auxiliary electrochemical cell 6 extends into the sampling chamber 5, as described above. A sensor head distal end cap shields the metallic mold until the cap burns, melts, or is otherwise removed. The sensor head distal end cap may comprise steel.

Figure 20:
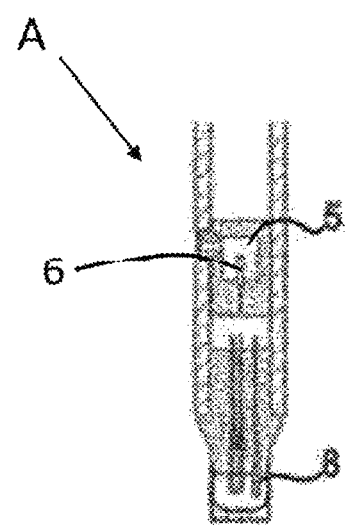
FIG. 20 is a side elevational view in cross-section of an immersion sensor comprising a sensor head located on the distal end of a carrier tube, the sensor head comprising a thermocouple and a primary electrochemical cell. The immersion sensor further comprises a sampling chamber located proximal to the sensor head, the sampling chamber comprising an auxiliary electrochemical cell extending into the sampling chamber, wherein the sampling chamber is formed in a refractory structure that is separate from, or not contiguous with, the sensor head.

FIG. 20 shows the immersion sensor A comprising a sensor head located on the distal end of a carrier tube, the sensor head comprising a thermocouple and also comprising a primary electrochemical cell 8. The thermocouple and the primary electrochemical cell 8 are located on and extend from the distal end of the sensor head. The immersion sensor A also comprises a separate refractory structure, not contiguous with the sensor head, comprising the sampling chamber 5. The separate refractory structure comprising the sampling chamber 5 is located proximal to the sensor head comprising the thermocouple and the primary electrochemical cell 8. The auxiliary electrochemical cell 6 extends into the sampling chamber 5, as described above. A sensor head distal end cap shields the thermocouple and the primary electrochemical cell 8 until the cap burns, melts, or is otherwise removed. The outer portion of the sensor head distal end cap may comprise cardboard; the inner portion of the sensor head distal end cap may comprise steel.

Figure 21:
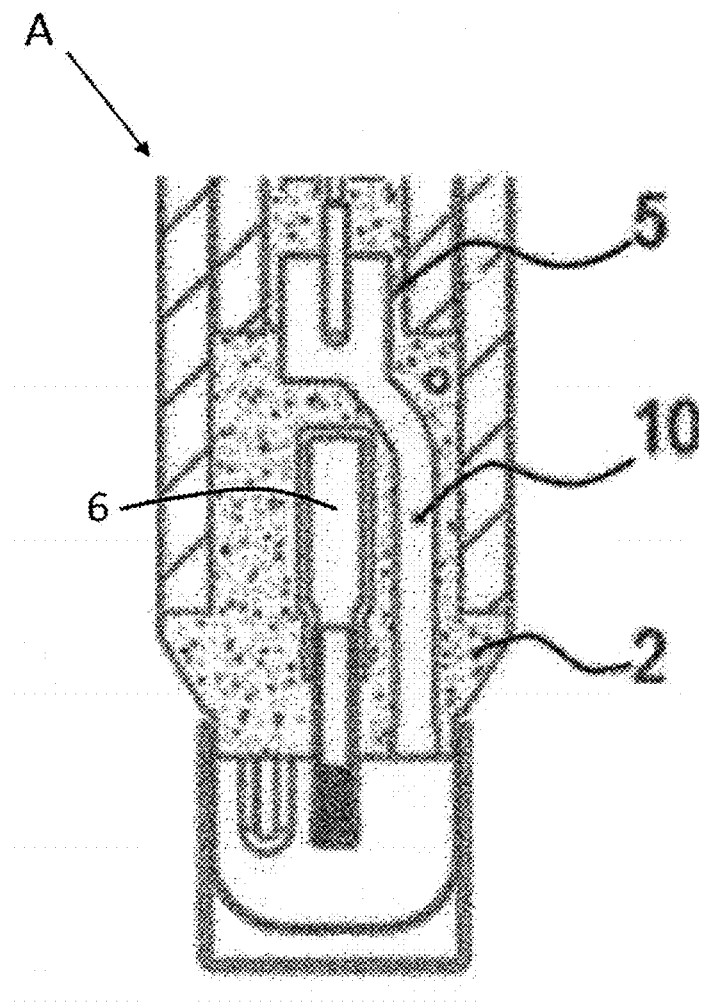
FIG. 21 is a side elevational view in cross-section of an immersion sensor comprising a sensor head located on the distal end of a carrier tube, the sensor head comprising an integrally-formed sampling chamber located proximal to the distal end of the sensor head, the sampling chamber comprising an auxiliary electrochemical cell extending into the sampling chamber, and the sensor head comprising an inlet channel extending between the sampling chamber and the distal end of the sensor head.

FIG. 21 shows the immersion sensor A comprising a sensor head located on the distal end of a carrier tube, the sensor head 2 comprising an integrally-formed sampling chamber 5 located proximal to the distal end of the sensor head 2. The auxiliary electrochemical cell 6 extends into the sampling chamber 5, as described above. The sensor head 2 also comprises an integrally-formed inlet channel 10 extending between the sampling chamber 5 and the distal end of the sensor head 2. A sensor head distal end cap shields inlet channel 10 until the cap burns, melts, or is otherwise removed. The outer portion of the sensor head distal end cap may comprise cardboard; the inner portion of the sensor head distal end cap may comprise steel.

Figure 22:
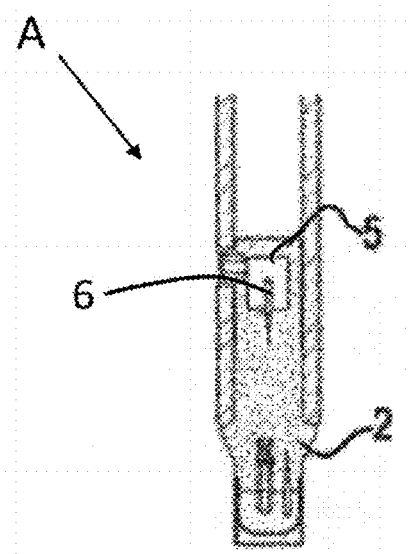
FIG. 22 is a side elevational view in cross-section of an immersion sensor comprising a sensor head located on the distal end of a carrier tube, the sensor head comprising an integrally-formed sampling chamber located proximal to the distal end of the sensor head, the sampling chamber comprising an auxiliary electrochemical cell extending into the sampling chamber.

FIG. 22 shows the immersion sensor A comprising a sensor head 2 located on the distal end of a carrier tube, the sensor head 2 comprising an integrally-formed sampling chamber 5 located proximal to the distal end of the sensor head 2. The auxiliary electrochemical cell 6 extends into the sampling chamber 5, as described above. The sensor head 2 also comprises an integrally-formed inlet channel 10 extending between the sampling chamber 5 and a lateral exterior surface of the immersion sensor A. The sensor head 2 also comprises a thermocouple and a primary electrochemical cell located on and extending from the distal end of the sensor head. A sensor head 2 distal end cap shields the thermocouple and the primary electrochemical cell until the cap burns, melts, or is otherwise removed. The outer portion of the sensor head distal end cap may comprise cardboard; the inner portion of the sensor head distal end cap may comprise steel.

Figure 23:
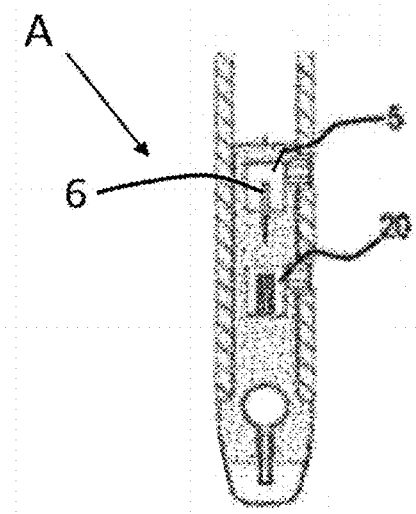
FIG. 23 is a side elevational view in cross-section of an immersion sensor comprising a sensor head located on the distal end of a carrier tube, the sensor head comprising a thermal analysis chamber integrally-formed in an intermediate portion of the sensor head located proximal to the distal end of the sensor head, the sensor head further comprising an integrally-formed sampling chamber located proximal to the thermal analysis chamber.

FIG. 23 shows the immersion sensor A comprising a sensor head located on the distal end of a carrier tube, the sensor head comprising a thermal analysis chamber 20 integrally-formed in an intermediate portion of the sensor head. The sensor head further comprises an integrally-formed sampling chamber 5 located proximal to the thermal analysis chamber 20. The auxiliary electrochemical cell 6 extends into the sampling chamber 5, as described above. The sensor head also comprises a metallic mold configured to collect samples of molten metal. The metallic mold is located distal to the thermal analysis chamber 20. A sensor head distal end cap shields the metallic mold until the cap burns, melts, or is otherwise removed. The sensor head distal end cap may comprise steel.

Various features and characteristics are described in this specification and illustrated in the drawings to provide an overall understanding of the invention. It is understood that the various features and characteristics described in this specification and illustrated in the drawings can be combined in any operable manner regardless of whether such features and characteristics are expressly described or illustrated in combination in this specification. The Inventors and the Applicant expressly intend such combinations of features and characteristics to be included within the scope of this specification, and further intend the claiming of such combinations of features and characteristics to not add new subject matter to the application. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new subject matter to the specification or claims, and will comply with written description, sufficiency of description, and added matter requirements (e.g., 35 U.S.C. § 112(a) and Article 123(2) EPC). The invention can comprise, consist of, or consist essentially of the various features and characteristics described in this specification.

Also, any numerical range recited in this specification includes the recited endpoints and describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements (e.g., 35 U.S.C. § 112(a) and Article 123(2) EPC).

The grammatical articles "one", "a", "an", and "the", as used in this specification, are intended to include "at least one" or "one or more", unless otherwise indicated or required by context. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the invention. Further, the use of a singular noun includes the plural, and the use of a plural noun includes the singular, unless the context of the usage requires otherwise.

LIST OF ELEMENTS

1. Carrier tube
2. Sensor head
3. Metallurgical vessel
4. Molten metal
5. Internal sampling chamber
6. Auxiliary electrochemical cell
7. Metallic mold
8. Electrochemical cell
9. Thermocouple
10. Inlet channel of sampling chamber 5
11. Protective cap or other temporary barrier structure
12. Internal volume of sampling chamber 5

13. Auxiliary electrode coating
14. Metallic coating (on at least a portion of an exterior surface of the auxiliary electrochemical cell 6)
15. Ceramic coating or glazing
16. Metallic coating (on at least a portion of an interior surface of the sampling chamber 5)
17. Deoxidizing material
18. Positive contact of the auxiliary electrochemical cell 6
19. Metallic electrode
20. Thermal analysis chamber integrally formed in the sensor head
100. Immersion sensor
101. Carrier tube
102. Sensor head
105. Integrally-formed sampling chamber of sensor head
110. Inlet channel
112. Distal end of carrier tube 101.
122. Distal end of sensor head.
124. Proximal end of sensor head
150. Separate refractory structure
152. Distal (lower) interior surface of sampling chamber 105
154. Proximal (upper) interior surface of sampling chamber 105
156. Lateral interior surfaces of sampling chamber 105
157. Distal (lower) end of refractory structure 150
159. Proximal (upper) end of refractory structure 150

What is claimed is:

1. An immersion sensor for determining the content of a chemical element in molten metal, the immersion sensor comprising:
    a sensor head located on the distal end of a carrier tube;
    a sampling chamber having an internal volume formed in a refractory structure;
    an inlet channel extending between the internal volume of the sampling chamber and a volume external to the immersion sensor; and
    an auxiliary electrochemical cell extending from an interior surface of the sampling chamber into the internal volume of the sampling chamber;
    wherein the immersion sensor is configured for the flow of molten metal from the external volume, through the inlet channel, into the internal volume of the sampling chamber, and into contact with the auxiliary electrochemical cell, wherein the inlet channel extends from a lateral interior surface of the sampling chamber to a lateral exterior surface of the sensor head, an aperture in the carrier tube being aligned with the inlet channel to provide the fluid communication between the internal volume of the sampling chamber and the volume external to the immersion sensor, and wherein the sampling chamber is disposed in an interior lumen of the carrier tube;
    wherein the sensor head comprises a refractory material of construction and the sampling chamber is integrally-formed in the sensor head and located proximal to a distal end of the sensor head.

2. The immersion sensor of claim 1, wherein the auxiliary electrochemical cell comprises an auxiliary electrode coating on at least a portion of an exterior surface of the auxiliary electrochemical cell.

3. The immersion sensor of claim 2, wherein the auxiliary electrode coating comprises a metal or metal oxide compound corresponding to Rai) the chemical element, wherein the immersion sensor is configured to determine the content of the chemical element in molten metal in the internal volume of the sampling chamber.

4. The immersion sensor of claim 1, wherein the auxiliary electrochemical cell comprises a metallic coating on at least a portion of an exterior surface of the auxiliary electrochemical cell.

5. The immersion sensor of claim 4, wherein the metallic coating covers at least a portion of an underlying auxiliary electrode coating on at least a portion of an exterior surface of the auxiliary electrochemical cell.

6. The immersion sensor of claim 1, wherein the sampling chamber is formed in a refractory material comprising molded foundry/casting sand.

7. The immersion sensor of claim 1, wherein the sampling chamber comprises a material of construction selected from the group consisting of metallic materials, ceramic materials, and cermet materials, and combinations of any thereof.

8. The immersion sensor of claim 1, wherein the sampling chamber comprises an internal ceramic coating on at least a portion of an interior surface of the sampling chamber.

9. The immersion sensor of claim 1, wherein the sampling chamber comprises an internal metallic coating on at least a portion of an interior surface of the sampling chamber.

10. The immersion sensor of claim 1, wherein the internal volume of the sampling chamber ranges from 5 $cm^3$ to 50 $cm^3$.

11. The immersion sensor of claim 1, wherein the sampling chamber comprises a deoxidizing material.

12. The immersion sensor of claim 11, wherein the deoxidizing material is selected from the group consisting of aluminum, aluminum alloys, titanium, titanium alloys, zirconium, and zirconium alloys, and combinations of any thereof.

13. The immersion sensor of claim 1, further comprising a temporary barrier structure located in the inlet channel.

14. The immersion sensor of claim 13, wherein the temporary barrier structure comprises a material selected from the group consisting of paper, cardboard, plastic, and metal, and combinations of any thereof.

15. The immersion sensor of claim 1, wherein the sampling chamber comprises an internal metallic coating on at least a portion of an interior surface of the sampling chamber, wherein the internal metallic coating is electrically connected to the auxiliary electrochemical cell and functions as a positive contact for operation of the auxiliary electrochemical cell.

16. The immersion sensor of claim 1, further comprising a metallic electrode extending from the interior surface into the internal volume of the sampling chamber, wherein the metallic electrode is electrically connected to the auxiliary electrochemical cell and functions as a positive contact for operation of the auxiliary electrochemical cell.

17. The immersion sensor of claim 1, further comprising a thermal analysis chamber integrally-formed in a proximal portion of the sensor head.

18. The immersion sensor of claim 17, wherein the thermal analysis chamber and the sampling chamber are integrally-formed in the same refractory material.

19. The immersion sensor of claim 18, wherein the thermal analysis chamber and the sampling chamber are integrally-formed in the sensor head.

20. The immersion sensor of claim 1, wherein the auxiliary electrochemical cell extends from a distal portion of the interior surface into the internal volume of the sampling chamber.

21. The immersion sensor of claim 1, wherein the auxiliary electrochemical cell extends from a proximal portion of the interior surface into the internal volume of the sampling chamber.

22. The immersion sensor of claim 1, wherein the auxiliary electrochemical cell extends from a lateral portion of the interior surface into the internal volume of the sampling chamber.

* * * * *